United States Patent [19]

Chu et al.

[11] Patent Number: 5,631,129
[45] Date of Patent: May 20, 1997

[54] TARGET NUCLEIC ACID AMPLIFICATION/DETECTION SYSTEMS AND METHODS FOR THE USE THEREOF

[75] Inventors: Barbara C. Chu, Del Mar; Gerald F. Joyce, Encinitas; Leslie E. Orgel, La Jolla, all of Calif.

[73] Assignee: The Salk Institute for Biological Studies, La Jolla, Calif.

[21] Appl. No.: 441,784

[22] Filed: May 16, 1995

Related U.S. Application Data

[63] Continuation of Ser. No. 74,261, Jun. 9, 1993, abandoned, which is a continuation of Ser. No. 710,433, Jun. 5, 1991, abandoned, which is a continuation-in-part of Ser. No. 279,817, Dec. 5, 1988, abandoned.

[51] Int. Cl.$^6$ .................. C12Q 1/68; C07H 21/02; C07H 21/04
[52] U.S. Cl. .................. 435/5; 435/6; 435/91.1; 435/91.2; 435/91.21; 435/91.3; 435/91.5; 435/91.51; 435/810; 436/501; 536/22.1; 536/23.1; 536/24.1; 536/24.3; 536/24.31; 536/24.32; 536/24.33; 536/25.3; 536/25.4; 935/77; 935/78
[58] Field of Search .................. 435/5, 6, 91.1, 435/91.2, 91.21, 91.3, 91.5, 91.51, 810; 436/501; 536/22.1, 23.1, 24.1, 24.3–24.33, 25.3, 25.4; 935/77, 78

[56] References Cited

U.S. PATENT DOCUMENTS 4,683,202  7/1987  Mullis ........................... 435/91
4,786,600  11/1988  Kramer et al. .................. 435/235

OTHER PUBLICATIONS

Miele, et al., "Autocatalytic Replication of a Recombinant RNA", J. Mol. Biol. 171, 281–295 (1983).
Feix, et al., "Primer Directed Initiation of RNA Synthesis Catalysed by Qβ Replicase", Biochem. Biophys. Res. Comm. 65, 503–509 (1975).
Vournakis, et al., "Synthesis of RNA Complementary to Rabbit Globin mRNA by Qβ Replicase", Biochem. Biophys. Res. Comm. 70, 774–782 (1976).
Miyake, et al., "Grouping of RNA Phages Based on the Template Specificity of Their RNA Replicases", Proc. Natl. Acad. Sci. USA, 68, 2022–2024 (1971).
Murakawa, et al. "Direct Detection of HIV-1 RNA from AIDS and ARC Patient Samples", DNA 7, 287–295 (1988).

*Primary Examiner*—Ardin H. Marschel
*Attorney, Agent, or Firm*—Pretty, Schroeder, Brueggemann & Clark; Stephen E. Reiter; Robert T. Ramos

[57] ABSTRACT

This invention relates to the use of functional reporter molecules in the detection and measurement of RNA sequences in a sample, as a determination, for example, of pathogenic disease existence or potential. The invention is predicated on the utilization of nucleotide sequences, one having a probe sequence linked to a sequence capable of initiating replication by an RNA-dependent RNA polymerase. The other is capable of hybridizing to a strand separated from the extension product of the first nucleotide sequence after hybridization to a specific target sequence. The extension product of the second hybridized nucleotide sequence serves as a template source for autocatalytic replication by the RNA-dependent RNA polymerase. The replication products are detected as a means for detection of nucleic acid sequences.

21 Claims, 1 Drawing Sheet

TARGET NUCLEIC ACID AMPLIFICATION/ DETECTION SYSTEMS AND METHODS FOR THE USE THEREOF

This application is a continuation application of Ser. No. 08/074,261, filed Jun. 9, 1993, now abandoned, which is a continuation application of Ser. No. 07/710,433, filed Jun. 5, 1991, now abandoned, which is a continuation-in-part application of Ser. No. 07/279,817, filed Dec. 5, 1988, now abandoned.

FIELD OF THE INVENTION

The present invention relates generally to nucleic acid target amplification compositions, methods and means, including assays and test kits, for detecting in an in vitro or ex vivo setting the presence of target RNA species, and by deduction the corresponding polypeptide that the RNA species encodes, in a biological sample. More particularly, the present invention relates to novel compositions and methods for producing, recombinant, autocatalytically replicatable RNAs which comprise a sequence of a target RNA segment of interest (or the complement thereof) such that the target sequence of interest may be amplified.

Among the applications in which the present invention finds use are in analyses of RNA sequences characteristic of a disease or pathogenic condition by in vitro or ex vivo nucleic acid probe hybridization assays of body fluids and tissues containing requisite target RNA.

BACKGROUND OF THE INVENTION

It is a goal in the nucleic acid probe art to detect various nucleic acid sequences in a biological sample, in which the sequences, as so-called target nucleic acid, are present, usually in small amounts relative to the wide variety of other nucleic acid species, including RNA, DNA or both. Thus, it is desirable to be able to detect the RNA encoding polypeptides that may be associated with diseases or pathological conditions, such as, for example, RNA of the genome of the human immunodeficiency virus. In addition to the detection of RNAs associated with such viruses, it is desirable to detect other RNAs characteristic of, for example, a disease or pathological condition, such as those transcribed from a defective gene, as in the case of hemophilia or sickle-cell anemia. Characteristically, the RNA associated with such a disease or condition is present, if at all, in very small amounts relative to total nucleic acid in a given biological sample, such as a sample of blood or other body fluid or a tissue sample of an individual to be tested.

The detection of such an RNA species requires such specificity and sensitivity that, if the RNA is present, it is detectable and measurable from amongst the wide variety of other nucleic acid species with which it is associated in a sample. Some of these non-target nucleic acid species may bear close homology, at least in isolated segments, to the target RNA. Further, as noted above, these target RNA species are very often found only in very minute amounts in the biological sample being tested. Yet, for proper diagnosis of the underlying disease state, it is essential that even small amounts of a target RNA be detectable if present.

Several approaches have been advanced for accomplishing reliable detection, in a biological sample, of a target nucleic acid present, if at all, in only a small amount and as only a minute fraction of total nucleic acid. In one approach, the amount of nucleic acid in the sample is not altered. Instead, a reporter system is employed whereby a large number of readily detectable molecules is produced for each molecule of target nucleic acid in the sample and the presence or quantity of the detectable molecules is measured. Such a reporter system is a signal-generating system associated with the target nucleic acid and produces a detectable signal representative of the number of molecules of target nucleic acid in a sample.

In another, fundamentally different, approach a target nucleic acid segment that is part of the target nucleic acid but not other nucleic acids in biological samples to be assayed, or the complement of such a target segment (i.e., the segment with the same size as, but sequence complementary to, that of the target segment), or both the target segment and its complement are selectively increased in copy number. That is, in a sample, the copy number of the target nucleic acid segment or its complement, or the copy numbers of both the target segment and its complement, are increased to a greater extent than the copy number of any other nucleic acid segment. This selective increase in copy number of a nucleic acid segment is referred to in the art as "amplification" of the segment. Once a target segment (also referred to herein, and in the art, as a "target sequence") or the complement of a target segment is amplified to a sufficient extent, it can be detected reliably by any of many techniques that have been developed in the nucleic acid probe art for the detection of nucleic acid segments, including techniques which involve the first approach, described above, that entails production of many readily detectable molecules for each molecule of target nucleic acid.

One method that has been developed for the amplification of a target segment is the so-called "polymerase chain reaction" ("PCR") method. This technique was reported by Saiki et al., Science 230, 1350 (1985) and Mullis et al., European Patent Application Publication Nos. 200362 and 201184 (See also U.S. Pat. Nos. 4,683,195 and 4,683,202), and particularly entails repeated cycles of (1) hybridizing to the 3'-end of a target nucleic acid sequence a first primer and to the 3'-end of the sequence complementary to the target sequence a second primer, (2) extending the primers with a polymerase, and (3) rendering single stranded the duplexes resulting from the chain extension reaction. This PCR procedure results in amplification of the target sequence and its complement exponentially with the number of cycles (i.e., as in a chain reaction).

Certain RNAs are known to be susceptible to autocatalytic replication by RNA-dependent RNA polymerases. Among the polymerases which are capable of such autocatalytic replication are bacterial phage RNA-dependent RNA polymerase such as Qβ replicase. Autocatalytically replicatable RNAs are said herein to have "template sequences" which means they have sequences that make them templates for replication by the polymerase. In the process, the RNA made from a template RNA (i.e., an RNA with a "template sequence") in the reaction catalyzed by the replicase is also replicatable RNA (i.e., also has a "template sequence"). Thus, in autocatalytic replication, the amount of replicatable RNA can increase exponentially. See Miele et al., *J. Molecular Biology* 171, 281 (1983).

Until recently it has not been appreciated that autocatalytic replication could be employed to provide convenient, broadly applicable, highly sensitive reporter systems for analyses of biological samples for the presence of particular nucleic acid sequences. A system in which probe for a target sequence is linked to an RNA capable of being replicated by Qβ replicase is described in U.S. Pat. No. 4,957,858, and by Chu et al., Nucleic Acids Research 14, 5591 (1986), the disclosures of which are expressly incorporated herein by reference. Thus, the invention described in U.S. Pat. No.

4,957,858 combines the art of replication of RNA with the art of nucleic acid hybridization probes by employing, as a signal producing moiety in a reporter system for detection of a target molecule, a replicatable RNA which is associated (through a probe, such as an oligonucleotide probe) with a target segment. A disadvantage of using such a nucleic acid hybridization assay having, as a reporter system, a replicatable RNA is that non-specific binding of a probe-replicatable RNA moiety to, for example, the walls of an assay tube can result in high levels of noise (i.e., low signal to noise ratios) and/or false positive readings.

It would be desirable to be able to combine the advantages of target nucleic acid amplification systems, where the target nucleic acid sequence itself is amplified, with the advantages of nucleic acid hybridization assays employing replicatable RNAs as a reporter system, while eliminating disadvantages of the former (such as the need for repeated thermal cycling steps) as well as disadvantages of the latter, such as non-specific binding of a reporter moiety which is capable of autocatalytic replication even in the absence of specific binding to a target sequence.

It is an object of the present invention to provide compositions and methods for detection of RNA target segments using a process that, in assuring the presence of the target sequence in the amplified product, avoids or at least substantially reduces the presence of low signal-to-noise ratios and false positives. It is a further object of the present invention to provide target RNA amplification compositions which utilize portions of autocatalytically replicatable RNAs and which result in the production of recombinant replicatable RNAs, such that autocatalytic replication of the recombinant RNAs results in amplification of a target nucleic acid of interest (i.e., a segment of the target RNA) which is foreign to the replicatable RNA.

It is thus an overall object of the present invention to meet the goals enumerated by the art and to provide selective means to meet disadvantages and problems encountered in the prior art. The methods and compositions of the present invention result in the production of recombinant, replicatable RNA molecules that are produced only where the necessary target nucleic acid sequence is present in the sample tested.

SUMMARY OF THE INVENTION

The present invention is predicated on the use in a novel manner of co-functioning RNA primers comprising first nucleotide sequence (also referred to herein as the first primer sequence) comprising (i) a first probe sequence suitable for hybridization with a segment of a target RNA sequence and (ii) extending in the 5'-direction from the 5'-end of the probe sequence, a first replication-initiation-complement sequence that is a sequence complementary to a sequence capable of initiating an autocatalytic replication process with a replicase. This first nucleotide sequence operates herein in conjunction with a second nucleotide sequence, said second nucleotide sequence (also referred to herein as the second primer sequence) comprising (i) a second probe sequence suitable for hybridization to the strand-separated extension product of the first nucleotide sequence, at "the opposite end of" the extension product from the first nucleotide sequence (by which is meant, more precisely, at a segment of said extension product 3' from the 3'-end of the first nucleotide sequence, which is at the 5'-end of the extension product), and (ii) extending in the 5'-direction from the 5'-end of the second probe sequence, a second replication-initiation-complement sequence that is also a sequence complementary to a sequence capable of initiating an autocatalytic replication process with a replicase. After hybridization of the first nucleotide primer sequence to target sequence (if any is present in a sample being assayed), the first sequence is extended in a chain extension reaction catalyzed by the replicase. Then the extension product is separated from the target nucleic acid and the second nucleic acid sequence is hybridized to the strand-separated extension product (which contains a sequence complementary to the target sequence) and extended in a second chain extension reaction by the replicase. The product of the second extension, as is or in strand-separated form if necessary, is then, in a process hereof of amplification, autocatalytically replicated in the presence of the replicase. The amplified replication products are then detected and measured using any of numerous techniques known per se by the art skilled (see, e.g., U.S. Pat. No. 4,957,858, issued Sep. 18, 1990).

The herein mentioned extension products are made in chain extension reactions that are catalyzed by an appropriate RNA-dependent RNA polymerase and carried out in the presence of the NTPs. In a preferred embodiment, said extension reaction(s) as well as the autocatalytic replication process are conducted with the same replicase, most preferably, Q-beta replicase.

See FIG. 1 hereof for a representative illustration of carrying out the target-sequence-recognition/amplification process aspect of the invention.

DETAILED DESCRIPTION OF THE INVENTION

Figure 1:
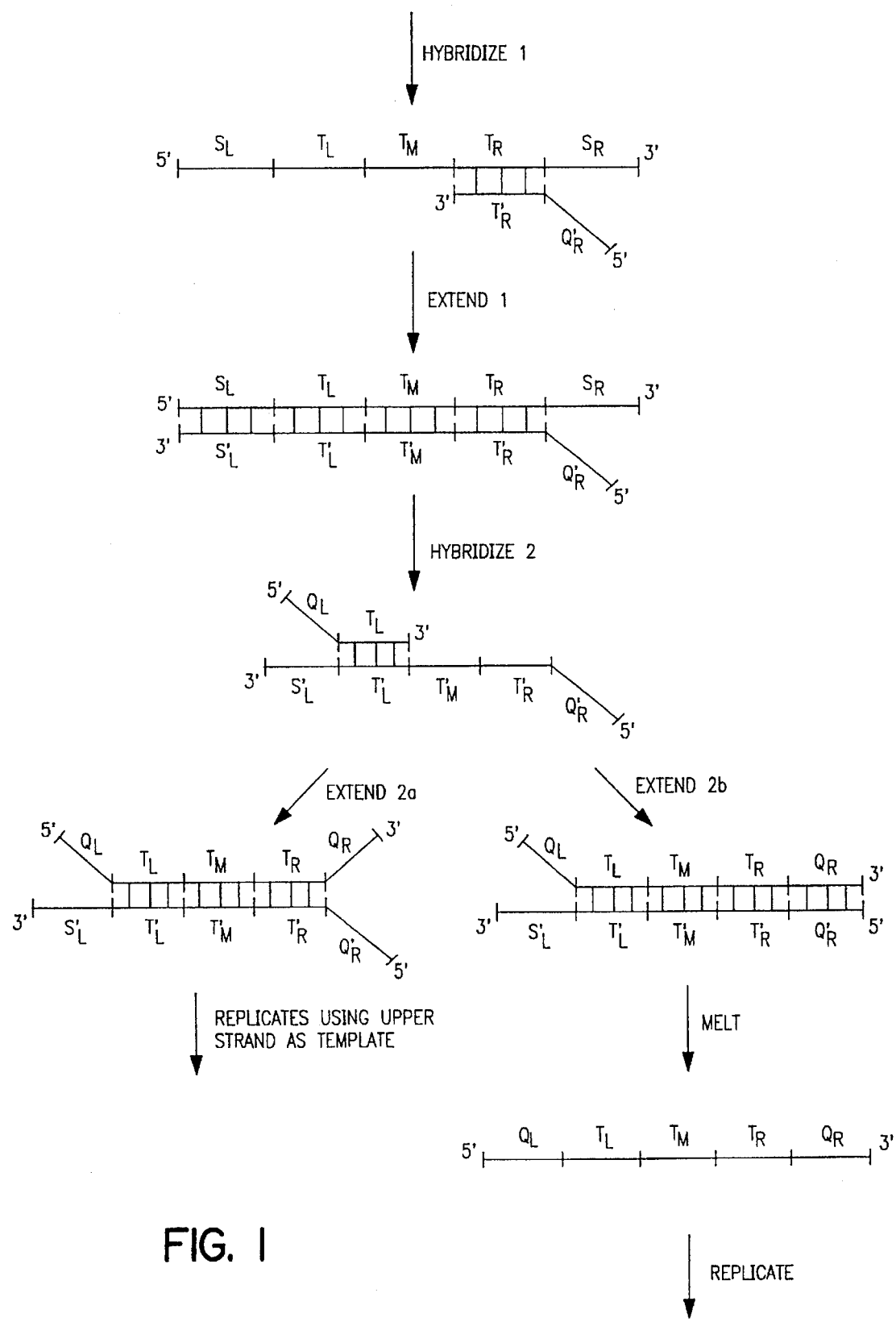
FIG. 1 depicts schematically an aspect of this invention, namely the steps hereof in target amplification using a single- or double-stranded RNA template for replication. Extension and amplification are carried out, e.g., with Q-beta RNA polymerase (replicase). T(target) is redesignated in segmented fashion as $T_L T_M T_R$. The primer sequences $Q_L T_L$ and $T_R 'Q'_R$ may be obtained by molecular cloning and subsequent in vitro transcription. The segment $T_M$ corresponds to the sequence of the target located between the probe portions of the primers. The required, recombinant template for autocatalytic replication amplification is obtained by hybridization, extension, rehybridization and re-extension as shown. Where the Q sequences represent Q-beta sequences, Q-beta replicase both chain extends and replicates, in turn.

In an aspect, the present invention entails co-functioning nucleic acid primers which are capable of forming a recombinant, autocatalytically replicatable RNA which has incorporated therein a target RNA sequence, said co-functioning primers comprising:

1) a first nucleic acid primer comprising (a) a first probe sequence which is capable of hybridizing to a target RNA sequence, in a sample containing same, and priming a primer-initiated extension reaction to produce a first primer extension product which contains an RNA sequence complementary to the sequence of the RNA target segment and (b) 5' from and contiguous with the 5'-terminal ribonucleotide of the first probe sequence, a first replication-initiation-complement sequence that (i) is one capable of being recognized by a replicase for initiation of an RNA-dependent RNA polymerase extension reaction from the 3'-end of the probe sequence utilizing target RNA sequence as a template and (ii) is a part, including the 5'-end, of an RNA that is autocatalytically replicatable by the replicase, the complement of said 5'-end being a replication-initiation sequence of a (+) strand or a (−) strand of a replicatable RNA which is capable of initiating RNA-dependent RNA polymerase-directed autocatalytic replication; and 2) a second nucleic acid primer comprising (a) a second probe sequence which is capable of hybridizing to said complementary target sequence of said first primer extension product and priming a primer-initiated extension reaction, with the first primer extension product as template; and (b) 5' from and contiguous with the 5'-terminal ribonucleotide of the second probe sequence, a second replication-initiation-complement sequence that (i) is one capable of being recognized by a replicase for initiation of an RNA-dependent RNA polymerase extension reaction from the 3'-end of the probe sequence utilizing target RNA sequence as a template and (ii) is a part, including the 5'-end, of an RNA that is autocatalytically replicatable by the replicase, the complement of said 5'-end being a replication-initiation sequence of a (+) strand or a (−) strand of the replicatable RNA which is capable of initiating RNA-dependent RNA polymerase-directed autocatalytic replication; provided that one primer has the 5'-end of a (+) strand and the other primer has a 5'-end of a (−) strand.

In another aspect, the present invention entails a method useful for the detection of at least one specific RNA target sequence in a sample containing nucleic acid, comprising:

hybridizing with said target RNA sequence under suitable conditions a nucleotide sequence comprising 1) a first nucleic acid primer comprising (a) a first probe sequence which is capable of hybridizing to a target RNA sequence, in a sample containing same, and priming a primer-initiated extension reaction to produce a first primer extension product which contains an RNA sequence complementary to the sequence of a segment of said RNA; and (b) 5' from and contiguous with the 5'-terminal ribonucleotide of the first probe sequence, a first replication-initiation-complement sequence that (i) is one capable of being recognized by a replicase for initiation of an RNA-dependent RNA polymerase extension reaction from the 3'-end of the probe sequence utilizing target RNA sequence as a template and (ii) is a part, including the 5'-end, of an RNA that is autocatalytically replicatable by the replicase, the complement of said 5'-end being a replication-initiation sequence of a (+) strand or a (−) strand of a replicatable RNA which is capable of initiating RNA-dependent RNA polymerase-directed autocatalytic replication;

chain extending said hybridized first nucleotide sequence to yield a first extension product;

strand separating the first extension product from the target RNA sequence;

hybridizing with said first extension product a second nucleic acid primer comprising (a) a second probe sequence which is capable of hybridizing to said complementary target sequence of said first extension product and priming a primer-initiated extension reaction, with the first primer extension product as template and (b) 5' from and contiguous with the 5'-terminal ribonucleotide of the second probe sequence, a second replication-initiation-complement sequence that (i) is one capable of being recognized by a replicase for initiation of an RNA-dependent RNA polymerase extension reaction from the 3'-end of the probe sequence utilizing target RNA sequence as a template and (ii) is a part, including the 5'-end, of an RNA that is autocatalytically replicatable by the replicase, the complement of said 5'-end being a replication-initiation sequence of a (+) strand or a (−) strand of a replicatable RNA which is capable of initiating RNA-dependent RNA polymerase-directed autocatalytic replication;

chain extending said hybridized second nucleotide sequence to yield a second extension product; and permitting operatively the second extension product of the previous step, optionally after strand separation, to undergo replication by contact with an appropriate RNA-dependent RNA polymerase; provided that one primer has the 5'-end of a (+) strand and the other primer has a 5'-end of a (−) strand.

The present invention is further directed to methods and means for assay systems based upon such principles and to kits incorporating components necessary for such assay methodology for detecting or measuring target RNA sequences, including in laboratory and clinical settings.

The present invention further embodies means for detecting and measuring the amount of the products of the autocatalytic replication and, thereby, also measuring the amount of target RNA present in a sample being analyzed. The products of the autocatalytic replication, which will contain replicase-recognizable sequence, may be detected and measured in a conventional manner as known to persons having ordinary skill in the art, such as, for example, via a chromophore moiety or a radioactive moiety incorporated in the course of the autocatalytic replication or by hybridization of a recombinant replicatable RNA comprising a target sequence (or complement thereof) with an oligonucleotide probe which is detectably labeled and comprises at least a subsequence of the target sequence or the complement of such a subsequence.

The present invention thus provides a method for the detection of at least one specific RNA target, in a sample containing nucleic acid, said RNA target comprising a target sequence and said method comprising detecting replicatable extension product, (or complement thereof), said replicatable product being the product of extension from a second ribonucleotide (i.e., RNA) sequence hybridized with a first RNA extension product strand-separated from the target RNA, which provides the template for synthesis of the first extension product from a first ribonucleotide sequence hybridized with the 3-end of the target sequence. In the method, said first ribonucleotide sequence comprises a first probe sequence complementary to a subsequence at the 3'-end of the target sequence; and, 5' from and contiguous with (i.e., linked through a single phosphate to) the 5'-terminal ribonucleotide of the probe sequence, a first replication-initiation-complement sequence that (a) is one capable of being recognized by a replicase for initiation of an RNA synthesis (i.e., chain extension) process from the 3'-end of the probe sequence utilizing target RNA sequence as a template and (b) is a part, including the 5'-end, of an RNA that is autocatalytically replicatable by the replicase. Further, said second ribonucleotide sequence comprises a second probe sequence that has the same sequence as a subsequence at the 5'-end of the target sequence (said 5'-subsequence not overlapping the 3'-subsequence of which the first probe sequence is the complement) and, therefore, a sequence that is complementary to that of a subsequence of the extension product from the first nucleotide sequence hybridized to target RNA, the 5'-end of said subsequence being 3' from the 3'-end of the first nucleotide sequence in said extension product; and 5'-from and contiguous with said second probe sequence, a second replication-initiation-complement sequence that (a) is one capable of being recognized by the replicase for initiation of an RNA synthesis (i.e., chain extension) process for the 3'-end of the second probe sequence utilizing complement of target RNA sequence as a template and (b) is a part, including the 5'-end, of an RNA that is autocatalytically replicable by the replicase, provided that the RNA which consists of the second replication-initiation-complement sequence joined at its 3'-end through a single phosphate to the 5'-end of the complement of the first replication-initiation-complement sequence (i.e., joined to the 5'-end of a replication-initiation sequence) is autocatalytically replicable by the replicase and provided further that an RNA which is made from said autocatalytically replicable RNA by inserting therein, between the 3'-end of said second replication-initiation-complement sequence and the 5'-end of the complement of said first replication-initiation-complement sequence, an RNA segment, is also autocatalytically replicable by the replicase. The replicatable extension product of said second nucleotide sequence (also referred to herein as a second extension product) functions, by autocatalytic replication catalyzed by the replicase, to amplify the target sequence. The replicatable extension product of the second nucleotide sequence as well as the complement of said extension product, by virtue of being an autocatalytically replicatable RNA comprising a sequence (or complement thereof) of the target RNA serves to amplify the target sequence (and complement thereof) and serves as a reporter molecule for the target sequence and associated target RNA.

In all respects, the present invention is directed to the novel application of the natural principles of hybridization of complementary RNA sequences, chain extension of RNA primers on RNA templates catalyzed by replicases (see, e.g., Vournakis et al., Biochem. Biophys. Res. Commun. 70, 774 (1976)), and autocatalytic replication of many RNAs, including recombinant RNAs, by replicases (see, e.g., Miele et al., supra; U.S. Pat. No. 4,786,600 the disclosure of which is hereby incorporated by reference) in order to amplify and render detectable and measurable target RNA sequences of target RNAs that may be present in a biological sample containing a mixture of nucleic acids.

The present invention contemplates the use of appropriate RNA-dependent RNA polymerase (replicase) enzymes that are capable both of chain extension and replication. A preferred embodiment employs Q-beta replicase enzyme to achieve both functions in a convenient, so-called single-pot reaction.

The present invention is also directed to assay systems and kits embodying same, useful for the detection of at least one specific RNA target sequence in a sample containing nucleic acid, after amplification of the target RNA sequence in accordance with the present invention. Kits would comprise a replicase, a first nucleotide sequence for carrying out the amplification process, as described above, a second nucleotide sequence for carrying out the amplification process, as described above, and compositions required to detect or provide detectability to the amplified product.

Reference is made to standard textbooks of molecular biology that contain definitions and methods and means for carrying out basic techniques of the present invention, such as RNA probe or primer preparation, including transcription of encoding DNA in an expression vector and the tailoring thereof so as to be suitable as such or when linked to other RNA for use as a probe herein; preparation of nucleotides with different functional sequences for use in hybridization; hybridization methodology including variations in stringency conditions for producing more or less hybridization certainty depending on the degree of homology of the primer to a target RNA sequence; identification, isolation or preparation of RNA polymerases capable of chain extension reactions and of recognizing said replicatable sequences referred to above; conditions conducive to the initiation and maintenance of extension reactions including use of RNA-dependent RNA polymerase and NTPs; the mechanism and methodology for autocatalytic (sometimes referred to herein as "induced") replication; and so forth. See, for example, Maniatis et al., Molecular Cloning: A Laboratory Manual, Cold Spring Harbor Laboratory, N.Y. 1982), and Colowick et al., Methods in Enzymology Volume 152, Academic Press, Inc. (1987), and the various references cited therein.

All of the aforecited publications are by this reference hereby expressly incorporated herein.

By the term "probe" in the present context is meant a RNA sequence that has sufficient homology with the target sequence such that under suitable hybridization conditions it is capable of hybridizing, that is binding to, the target sequence. A typical probe is at least about 10 nucleotides in length, and most preferably is of approximately 25 or more nucleotide bases in length, and in its most preferred embodiments, it shares identity or very high homology with the target sequence. See, for example, EPA 128042 (publd. 12 Dec. 1984).

The RNA primer extension react fort to produce an RNA—RNA duplex is known. (See, Vournakis et al., supra.; Feix and Hake, Biochem. Biophys. Res. Comm. 65, 503–509 (1975)). RNA-dependent RNA polymerases such as Qβ replicase are capable of extending an RNA-primed extension reaction at least about 100 to about 500 nucleotides or more along a foreign RNA template and at least about 4000 nucleotides or more where the RNA is a Qβ-related RNA. (The Qβ virus RNA is over 4200 nucleotides in length.) In accordance with preferred embodiments of the present invention, the probe segments of the first and the second primers are selected so as to give an interprimer distance of at least about 10 to about 20 nucleotides and more preferably at least about 50 to about 200 or more nucleotides to permit detecting, by a nucleic acid hybridization assay, recombinant replicatable RNA produced in the amplification process of the invention. The interprimer distance corresponds to the segment denoted $T_M$ in FIG. 1. It is most preferred to utilize at least a portion of the $T_M$ subsegment of a recombinant replicatable RNA to detect the presence and/or measure the amount of target RNA initially present in a biological sample subjected to the amplification method of the invention inasmuch as this sequence is unique to said recombinant RNA (i.e., it is not a part of the first primer or the second primer of the invention). Notwithstanding this preference, recombinant, replicatable RNAs may be probed along sequences which are in common with the first or the second primer used in the method of the invention, where the nucleic acids from the amplification reaction mixture are size-separated (e.g., by SDS-PAGE electrophoresis) prior to the detection step.

The term "replication-initiation-complement sequence", as used herein, means the subsegment of the defined cofunctioning nucleotide primer sequences contiguous with (linked through a phosphodiester bond to) the 5'-end of probe subsegment, which is a portion of a replicatable RNA including its 5'-end. The complement of such a 5'-end sequence is a 3'-end of a replicatable RNA which is capable of initiating autoreplication.

Recognition of a strand of replicatable RNA as being competent to initiate autoreplication is determined by the sequence at the 3'-end of replicatable RNA. (See, Nishihara et al., J. Biochem. 93, 669–674 (1983)). Because an exponential increase in the number of molecules of replicatable RNA is achieved where each of the complementary strands has a 3'-end which is recognizable by replicase and because the recombinant replicatable RNAs of the present invention are produced, initially, by chain extension reactions which proceed in a 5' to 3' direction, it will be seen that the subsegments of the cofunctioning sequences of the present invention which are a portion, including the 5'-end, of a replicatable RNA encode (as their complement) a 3'-end portion including a replication-initiation sequence. Thus, as used herein with respect to the cofunctioning sequences, reference to "a part of an RNA that is autocatalytically replicatable by a replicase, including the 5'-end thereof" refers more precisely to a segment of a replicatable RNA, the complement of which comprises a sequence capable of initiating RNA-dependent RNA polymerase-directed autocatalytic replication. In other words, the complement of the defined 5'-end of a primer of the invention is also a 3'-end of a recombinant replicatable RNA. Complementary strands of a replicatable RNA are conventionally designated as the (+) strand and the (−) strand. Each of the complementary strands is independently autoreplicable provided the 3'-end thereof is intact and capable of initiating replication. Because the first primer of the invention must act as the template for forming a second extension product of the invention (which is a recombinant replicatable RNA), it will be seen that one of the cofunctioning primers should be a (+) strand of a replicatable RNA and the other primer should be a (−) strand of the replicatable RNA. In other words, the primers of the invention comprise 5'-ends from complementary strands of a replicatable RNA.

In addition to having a 3'-end which is capable of initiating autocatalytic replication, replicatable RNAs, including recombinant replicatable RNAs, have a replicase binding sequence capable of binding replicase. The nucleotide sequence of the replicase binding site of RNAs specific for Q beta replicase, and likely other replicases, comprises an intramolecularly duplexed region. Such structural organization would account for ability of replicases to distinguish replicatable RNAs from other nucleic acids (for purposes of autocatalytic replication). (As discussed above, replicases can polymerize RNA-dependent RNA polymerization of primed RNA strands which are not replicatable RNAs). For autocatalytic replication Q beta replicase, for example, binds to a sequence in the internal region of the nucleotide sequence of a replicatable RNA. One of the cofunctioning sequences of the present invention therefore comprises, in addition to a sequence, the complement of which is capable of initiating autocatalytic replication, a sequence which is a replicase binding site.

The replicase binding site of replicatable RNAs is highly conserved. Significant homology exists, for example, between the internal nucleotide sequence in Q beta (−) RNA (nucleotides 81 to 126) and MDV-1 (+) RNA (nucleotides 84 to 129) which sequences comprise the Q beta replicase binding site. (See, Nishihara et al., supra.) Those persons having ordinary skill in the art can readily identify the replicase binding site of RNAs which are recognized by a replicase such as, for example, Q beta replicase, by utilizing knowledge of the sequences of highly conserved replicase binding sites of autoreplicatable RNAs, computer generated comparisons of nucleotide sequences and predicted secondary structures of autoreplicatable RNAs, replicase-RNA binding analyses and other techniques which are known in the art.

A nucleotide sequence corresponding to the replicase binding site may be a part of either the first nucleotide sequence or the second nucleotide sequence of the present invention. Where the replicase binding site is carried by a subsegment of the first nucleotide sequence, said subsegment comprises a part, including the 5'-end and the replicase binding site, of a replicatable RNA. Correspondingly, where the replicase binding site is carried by a subsegment of the second nucleotide sequence of the invention, said subsegment comprises a part, including the 5'-end and the replicase binding site of a replicatable RNA.

The 5'-end-containing subsegments of the cofunctioning "primers" may be of any length which does not interfere with the ability of such primer to hybridize to a target sequence and to be extended and which, of course, is able to itself act as a template for a functional replication-initiation sequence. At least one, preferably exactly one, of the cofunctioning primers includes a replicase binding site located 5' to the probe sequence and within said segment of a primer which has a sequence of a replicatable RNA including the 5'-end. Preferably the primer having a replicase binding site comprises a sequence of a replicatable RNA which extends from the 5'-most nucleotide in the 3' direction up to a position which includes at least the sequence of a replicase binding site.

An autocatalytically replicatable RNA may comprise additional duplexed regions besides the replicase binding site. Such duplexed regions, where they occur internally, have associated therewith single stranded sequences which are known in the art as "hairpin turns." In accordance with the present invention, it is preferred to select the nucleotide position at which the respective 5'-end-containing subsegments of the first and second primers of the invention terminate so that the recombinant replicatable RNAs of the present invention form such intramolecular duplexes to the extent necessary to maintain autocatalytic replicatability. Thus, in preferred embodiments of the present invention, the 5'-end-containing subsegment should have a sequence of a replicatable RNA which extends from the 5'-end to a nucleotide position of the replicatable RNA which is near a single stranded region of the replicatable RNA thereof and more preferably is in a single stranded region. Most preferably, the 5'-end subsegment extends to a nucleotide position which is in a hairpin turn region of such replicatable RNA, so that a recombinant RNA of the present invention has the target sequence (or complement thereof) inserted in such a haripin turn region which does not significantly interfere with duplex formation affecting autoreplication function. Such a subsegment should not be terminated in the replicase binding site or replication-initiation sequence. In an especially preferred embodiment of the present invention, the cofunctioning pair of primers respectively have complementary 5'-end-containing subsegments of a replicatable RNA which terminate at or near the hairpin turn region corresponding to the region defined by nucleotides 60–63 of MDV-1 (+) RNA, including the corresponding region of MDV-1 (−) RNA, such that a recombinant RNA produced in accordance with this embodiment of the present invention has a target sequence (or complement thereof) inserted at a region corresponding to this hairpin turn region of MDV-1 RNA.

Reference herein to bacteriophage Qβ is not limited to any particular variant or mutant or population thereof. Such reference, unless otherwise specifically limited, is to any variant, mutant or population which, upon infection therewith of E. coli susceptible to bacteriophage Qβ infection, is capable of causing production of an RNA-dependent RNA-polymerase or any polymerase acting as a replicase and its associated nucleic acid substrate.

For other phages which, upon infection of bacteria susceptible to infection therewith, produce RNA-dependent RNA polymerases, and associated replicatable RNAs capable of being autocatalytically replicated in vitro, which can be employed in the present invention, see, e.g., Miyake et al., *Proc. Natl. Acad. Sci. (U.S.A.)* 68, 2022 (1971).

Provided that the concentration of replicase remains above the concentration of template RNA, and that ribonucleoside-5'-triphosphate concentration does not become limiting, the concentration of template RNA will increase exponentially with time during replicase-catalyzed RNA replication. After template RNA concentration equals or exceeds replicase concentration, as long as ribonucleoside-5'-triphosphate concentration does not become limiting, the concentration of template RNA will increase linearly with time. See, e.g., Kramer, et al. (1974), supra. It has been found that, under the conditions for replicase-catalyzed replication, the MDV-1 RNA there exemplified doubled in concentration every 36 seconds, until template concentration exceeded enzyme concentration.

The concentration of template RNA, in a replicase-catalyzed replication reaction system after a given time for reaction, will be related to the initial concentration of template RNA. If, at all times during the replication reaction, the concentration of replicase exceeds that of template (and ribonucleoside-5'-triphosphate concentration does not become limiting), the log of concentration of template RNA at the conclusion of the reaction will be directly proportional to the log of the initial concentration of template (at the start of the reaction). After replicase concentration falls below template concentration, as long as ribonucleoside-5'-triphosphate concentration does not become limiting, the concentration of template at the conclusion of reaction is directly proportional to the log of the initial concentration of template. Further, the time required for a reaction to reach the point at which template concentration equals replicase concentration is proportional to the negative log of the initial concentration of template.

By allowing the replication reaction to proceed for longer times, greater sensitivity can be achieved.

Assays according to the invention may be carried out simultaneously, under conditions as nearly alike as possible, on both test samples, which are being tested for target, and control samples. As understood in the art, control samples are similar to test samples but are known to contain either no target or a known quantity of target. A control with no target establishes the "background," below which it is not possible to distinguish samples which contain target from those which do not. By comparing the amount or concentration of replicated replicative RNA produced in an assay of a test sample with the amount or concentration produced with control samples assayed simultaneously, the presence of target in test sample at a level above background can be determined. If control samples with a range of known concentrations of target are employed, the concentration of target in a test sample can be estimated.

A sample on which the assay method of the invention is carried out can be a raw specimen of biological material, such as serum or other body fluid, tissue culture medium or food material. More typically, the method is carried out on a sample which is a processed specimen, derived from a raw specimen by various treatments to remove materials that would interfere with detection of target, such as by causing non-specific binding of affinity molecules. Methods of processing raw samples to obtain a sample more suitable for the assay methods of the invention are well known in the art.

RNA resulting from the replication process can be made fluorescent by employing a T4 RNA ligase catalyzed reaction to append nucleotides modified to be fluorescent to the 3'-end of replicative RNA. See Cosstick et al., *Nucl. Acids Res.* 12, 1791 (1984). The fluorescence of the resulting RNA can be employed to detect the RNA by any of several standard techniques.

Among still other methods that can be used to detect replicated RNA are those wherein a reporter substance, that binds specifically with nucleic acid, is added to the system in which the replication has taken place, or to the medium, such as a positively charged support such as ECTEOLA paper, on which replicated RNA has been isolated, and signal from the reporter substance measured. Such substances include: chromogenic dyes, such as "stains all" (Dahlberg et al., *J. Mol. Biol.* 41, 139 (1969); methylene blue (Dingman et al., *Biochemistry* 7, 659 (1968), and silver stain (Sammons et al., *Electrophoresis* 2, 135 (1981); Igloi, *Anal. Biochem.* 134, 184 (1983)); fluorogenic compounds that bind to RNA—for example, ethidium bromide (Sharp et al., *Biochemistry* 12, 3055 (1973); Bailey et al., *Anal. Biochem.* 70, 75 (1976); and fluorogenic compounds that bind specifically to RNAs that are templates for replication by Qβ replicase—for example, a phycobiliprotein (Oi et al., *J. Cell Biol.* 93, 981 (1982); Stryer et al., U.S. Pat. No. 4,520,110) conjugated to the viral subunit of Qβ replicase.

The following examples illustrate a model system of this invention:

EXAMPLES

Exemplified is the use of Q-beta polymerase and an RNA substrate that is replicatable by said polymerase in order to amplify a target RNA sequence that is contained within the RNA substrate. Q-beta replicase is an RNA-dependent RNA polymerase that recognizes characteristic structural elements at the 3'-end of an RNA substrate and subsequently produces a complementary copy of the substrate. If the complementary copy also has the requisite structural elements at its 3'-end, then it too can be recognized and copied by Q-beta replicase, resulting in an autocatalytic reaction cycle that exponentially amplifies the substrate sequence Q-beta replicase is able to bypass its normal initiation specificity and extend complementary synthesis from the 3'-end of a suitable oligonucleotide primer (Feix, G. & Hake, H. *Biochem. Biophys. Res. Comm.* 65, 503–509, 1975). The reaction generates mainly partial-length cRNAs and a considerable amount of non-specific RNAs (Vournakis et al., *Biochem. Biophys. Res. Comm.* 70, 774–782, 1976), and thus is not suitable for replication. However, it could be used to extend an RNA primer through a short target region of about 20–500 nucleotides and more preferably from about 50 to about 200 nucleotides.

Preparation of Primers

Two RNA primers are prepared by in vitro transcription of a suitably constructed recombinant DNA. The first primer contains the first 157 nucleotides (at the 5'-end) of the minus-strand of Q-beta MDV-1 RNA followed by 10–50 nucleotides that are complementary to the target RNA over a region extending 5' from the 3' end (i.e., "just downstream from") of the site of interest (i.e., the target sequence). The second primer contains the first 61 nucleotides (at the 5' end) of the plus-strand of Q-beta MDV-1 RNA followed by 10–50 nucleotides that are identical to the target RNA over a region extending 3' from the 5'-end of the target sequence.

Hybridization and Primer Extension

A control template DNA, such as pT7-0 (U.S. Biochemical), is used to prepare suitable RNA transcripts that can serve as a target for detection. 1 fg, 10 fg, 100 fg, 1 pg, 10 pg, or 100 pg of the RNA transcript ($10^{-5}$ fmol - $10^{-3}$ pmol) is diluted to 50 µl volume to give a final solution containing 100 mM Tris. HCl (pH 7.5), 22 mM $MgCl_2$, 2 mM $Na_2EDTA$, and 1 mM (each) of the four NTPs. To this solution is added a 25 µl volume containing 2 ng (approx. 1 nM) of each of the two RNA primers. The mixture is heated to 70° C. for 1 min and then quick-cooled on ice. A 25 µl volume containing 2 µg of Q-beta replicase is added, and the mixture is incubated at 37° C. for 10 min. The mixture is again heated to 70° C. for 1 min and quick-cooled on ice. A second 25 µl volume containing 2 g of Q-beta replicase is added, and the mixture is again incubated at 37° C. for 10 min.

Amplification of Target RNA

The second primer-extension product is optionally released from the template by heating to 70° C. for 1 min and quick-cooling on ice. If this step is included, then a third 25 µl volume containing 2 µg of Q-beta replicase in a solution containing 50 mM Tris.HCl (pH 7.5), 11 mM $MgCl_2$, 1 mM $Na_2EDTA$, and 0.5 mM (each) of the four NTPs must be added. In either case, amplification of the target RNA then proceeds autocatalytically by incubating at 37° C. for 20 min. The resulting mixture can then be assayed for the production of MDV-1 RNA which contains an insert that corresponds to the desired target sequence.

Detection of Replicated RNA

The amount of RNA is determined by its intrinsic UV absorbance (e.g. as by the contact photoprinting method of Kutateladze et al., *Anal. Biochem.* 100, 129 (1979)). Alternatively, the RNA is visualized on ETEOLA paper. Aliquots (of equal volume) of replication reaction are transferred with 13, 48 or 96-fingered aliquotter to sheets of diethylaminoethyl cellulose paper. The sheets are then washed at room temperature in a solution of 200 mM NaCl, 300 mM ammonium acetate pH 6 to remove ribonucleoside triphosphates not incorporated into RNA. The sheets are then stained with 0.3 μg/ml of ethidium bromide. (Sharp et al., *Biochemistry* 12, 3055 (1973); Bailey et al., *Anal. Biochem* 70, 75 (1976).

Finally the fluorescence from individual blots is measured by any of several known techniques. Fluorescence intensity from a stained blot above that from control blots indicates the presence of target. Other staining materials can be employed in place of ethidium bromide. These include methylene blue (Dingman and Peacock, *Biochemistry* 7, 659 (1968)), silver stain (Sammons, et al., *Electrophoresis* 2, 135 (1981)) or phycobiliprotein Qβ replicase conjugate (Oi et al., *J. Cell Biol.* 93, 981 (1982)).

While the invention has been described with some specificity, modifications apparent to those with ordinary skill in the art may be made without departing from the spirit of the invention.

Various features of the invention are set forth in the following claims.

We claim:

1. Co-functioning nucleic acid primers useful for forming a recombinant, autocatalytically replicatable RNA having incorporated therein a target RNA sequence, said co-functioning primers comprising:

(1) a first nucleic acid primer comprising:

(a) at its 5'-end, a first portion of an autocatalytically replicatable RNA, wherein the complement of said first portion is a segment of an autocatalytically replicatable RNA which comprises the 3'-end of an autocatalytically replicatable RNA which is capable of RNA-dependent RNA polymerase-directed autocatalytic replication, and wherein said first portion is a segment of a (+) strand or a (−) strand of an autocatalytically replicatable RNA, including the 5'-end; and (b) at its 3'-end, a first probe sequence which is capable of hybridizing to a segment of a target RNA sequence, and priming an extension reaction, using the target RNA sequence as template, to produce a first primer extension product which includes an RNA sequence complementary to the target RNA sequence; and (2) a second nucleic acid primer comprising:

(a) at its 5'-end, a second portion derived from the opposite strand of said autocatalytically replicatable RNA, wherein the complement of said second portion comprises the 3'-end of an autocatalytically replicatable RNA which is capable of RNA-dependent RNA polymerase-directed autocatalytic replication, and wherein said second portion is a segment of a (+) strand or a (−) strand of said autocatalytically replicatable RNA, including the 5'-end; and (b) at its 3'-end, a second probe sequence which is capable of hybridizing to a segment of said RNA sequence complementary to the target RNA sequence and priming an extension reaction, using the first extension product as template, to produce a second primer extension product which is autocatalytically replicatable RNA having incorporated therein a target RNA sequence;

provided that either the first or second portion of said autocatalytically replicatable RNA is derived from the (+) strand and the other portion of said autocatalytically replicatable RNA is derived from the (−) strand of the same autocatalytically replicatable RNA, and further provided that one of said cofunctioning primers includes a replicase binding site.

2. Nucleic acid primers according to claim 1 wherein the first and the second portions of said autocatalytically replicatable RNA correspond to complementary strands of an autocatalytically replicatable RNA which is recognized by Q-beta replicase.

3. Nucleic acid primers according to claim 2 wherein one portion of said autocatalytically replicatable RNA terminates at a nucleotide position selected from the group consisting of nucleotide positions 60, 61, 62, and 63 of MDV-1(+) RNA, and the other portion of said autocatalytically replicatable RNA terminates at a position which is the complement of a nucleotide position selected from the group of positions 60, 61, 62, and 63 of MDV-1(+) RNA.

4. Nucleic acid primers according to claim 1, 2, or 3, wherein the first probe sequence is complementary to a segment of a human immunodeficiency virus.

5. Nucleic acid primers according to claim 1,2, or 3, wherein the first probe sequence is complementary to a sequence of a defective gene or a defective transcript of a normal gene.

6. An extension product of either the first or second nucleic acid primer according to claim 1 after its hybridization with the target sequence from a sample.

7. A method for determining whether at least one specific RNA target sequence is present in a nucleic acid containing sample, said method comprising priming a replicatable extension product and detecting the presence or absence of said product wherein detection of said replicatable extension product is indicative of the presence of said specific RNA target sequence in the sample, said extension product being an extension from a second nucleic acid primer hybridized with a strand separated from a first extension product that contains a sequence of a first nucleic acid primer hybridizable with a target RNA sequence, said replicatable extension product functioning as a reporter molecule for said target, wherein said first nucleic acid primer comprises:

(a) at its 5'-end, a first portion of an autocatalytically replicatable RNA, wherein the complement of said first portion is a segment of an autocatalytically replicatable RNA which comprises the 3'-end of an autocatalytically replicatable RNA which is capable of RNA-dependent RNA polymerase-directed autocatalytic replication, and wherein said first portion is a segment of a (+) strand or a (−) strand of an autocatalytically replicatable RNA, including the 5'-end; and (b) at its 3'-end, a first probe sequence which is capable of hybridizing to a segment of a target RNA sequence, and priming an extension reaction, using the target RNA sequence as template, to produce a first primer extension product which includes an RNA sequence complementary to the target RNA sequence; and wherein said second nucleic acid primer comprises:

(a) at its 5'-end, a second portion derived from the opposite strand of said autocatalytically replicatable RNA, wherein the complement of said second portion comprises the 3'-end of an autocatalytically replicatable RNA which is capable of RNA-dependent RNA polymerase-directed autocatalytic replication, and wherein said second portion is a segment of a (+) strand or a (−) strand of said autocatalytically replicatable RNA, including the 5'-end; and (b) at its 3'-end, a second probe sequence which is capable of hybridizing to a segment of said RNA sequence complementary to the target RNA sequence and priming an extension reaction, using the first extension product as template, to produce a second primer extension product which is autocatalytically replicatable RNA having incorporated therein a target RNA sequence;

provided that either the first or second portion of said autocatalytically replicatable RNA is derived from the (+) strand and the other portion of said autocatalytically replicatable RNA is derived from the (−) strand of the same autocatalytically replicatable RNA, and further provided that one of said cofunctioning primers includes a replicase binding site.

8. A method according to claim 7 including the additional step of detecting replicatable product by permitting said product to replicate.

9. A method according to claim 8 wherein said replication is effected by contacting replicatable product with replicase enzyme.

10. A method according to claim 9 wherein said replicase enzyme is Q-beta replicase.

11. A method for determining whether at least one specific RNA target sequence is present in a nucleic acid containing sample, said method comprising:

hybridizing, under suitable conditions, said RNA target sequence with a first nucleic acid primer comprising:

(a) at its 5'-end, a first portion of an autocatalytically replicatable RNA, wherein the complement of said first portion is a segment of an autocatalytically replicatable RNA which comprises the 3'-end of an autocatalytically replicatable RNA which is capable of RNA-dependent RNA polymerase-directed autocatalytic replication, and wherein said first portion is a segment of a (+) strand or a (−) strand of an autocatalytically replicatable RNA, including the 5'-end; and (b) at its 3'-end, a first probe sequence which is capable of hybridizing to a segment of a target RNA sequence, and priming an extension reaction, using the target RNA sequence as template, to produce a first primer extension product which includes an RNA sequence complementary to the target RNA sequence;

chain extending said hybridized nucleic acid primer, strand separating the resulting extension product, hybridizing the strand separated in the previous step containing the sequence that is the complement of one susceptible to replication with a second nucleic acid primer, said second nucleic acid primer comprising:

(a) at its 5'-end, a second portion derived from the opposite strand of said autocatalytically replicatable RNA, wherein the complement of said second portion comprises the 3'-end of an autocatalytically replicatable RNA which is capable of RNA-dependent RNA polymerase-directed autocatalytic replication, and wherein said second portion is a segment of a (+) strand or a (−) strand of said autocatalytically replicatable RNA, including the 5'-end; and (b) at its 3'-end, a second probe sequence which is capable of hybridizing to a segment of said RNA sequence complementary to the target RNA sequence and priming an extension reaction, using the first extension product as template, to produce a second primer extension product which is autocatalytically replicatable RNA having incorporated therein a target RNA sequence;

provided that either the first or second portion of said autocatalytically replicatable RNA is derived from the (+) strand and the other portion of said autocatalytically replicatable RNA sequence is derived from the (−) strand of the same autocatalytically replicatable RNA, and further provided that one of said cofunctioning primers includes a replicase binding site, chain extending said hybridized second nucleic acid primer, permitting the second extension product of the previous step, optionally after strand separation, to undergo replication by contacting with an appropriate RNA-dependent RNA polymerase, and detecting the presence or absence of replication product, wherein detection of said replication product is indicative of the presence or said specific RNA target sequence in the sample.

12. The method according to claim 11 wherein said RNA-dependent RNA polymerase is Q-beta replicase.

13. The method according to claim 12 or 11, wherein the replicatable products are measured in a standardized manner so as to measure the amount of target sequence contained in a sample of nucleic acid.

14. The method according to claim 12 or 11, wherein said target sequence is disposed within a nucleic acid sequence associated with the characteristics of a genetic or pathogenic disease or condition.

15. The method according to claim 14 wherein said nucleic acid sequence is a RNA segment corresponding to a human immunodeficiency virus.

16. The method according to claim 14 wherein said nucleic acid sequence is a transcript of a defective gene or a defective transcript of a normal gene.

17. The method according to claim 12 or 11, wherein said replicatable products are labeled prior to detection.

18. The method according to claim 17 wherein said products are radio-labeled.

19. The method according to claim 17 wherein said products are chromophore labeled.

20. The method according to any one of claims 12 or 11 wherein said detecting is conducted by hybridization of the replicated products with an a hybridization probe, optimally labeled, which is a subsequence of said target sequence.

21. A kit useful for the detection of at least one specific RNA target sequence in a sample containing nucleic acid, said kit comprising:
   (1) a first nucleic acid primer comprising:
      (a) at its 5'-end, a first portion of an autocatalytically replicatable RNA, wherein the complement of said first portion is a segment of an autocatalytically replicatable RNA which comprises the 3'-end of an autocatalytically replicatable RNA which is capable of RNA-dependent RNA polymerase-directed autocatalytic replication, and wherein said first portion is a segment of a (+) strand or a (−) strand of an autocatalytically replicatable RNA, including the 5'-end; and
      (b) at its 3'-end, a first probe sequence which is capable of hybridizing to a segment of a target RNA sequence, and priming an extension reaction, using the target RNA sequence as template, to produce a first primer extension product which includes an RNA sequence complementary to the target RNA sequence; and
   (2) a second nucleic acid primer comprising:
      (a) at its 5'-end, a second portion derived from the opposite strand of said autocatalytically replicatable RNA, wherein the complement of said second portion comprises the 3'-end of an autocatalytically replicatable RNA which is capable of RNA-dependent RNA polymerase-directed autocatalytic replication, and wherein said second portion is a segment of a (+) strand or a (−) strand of said autocatalytically replicatable RNA, including the 5'-end; and
      (b) at its 3'-end, a second probe sequence which is capable of hybridizing to a segment of said RNA sequence complementary to the target RNA sequence and priming an extension reaction, using the first extension product as template, to produce a second primer extension product which is autocatalytically replicatable RNA having incorporated therein a target RNA sequence;
   provided that either the first or second portion of said autocatalytically replicatable RNA is derived from the (+) strand and the other portion of said autocatalytically replicatable RNA is derived from the (31) strand of the same autocatalytically replicatable RNA, and further provided that one of said cofunctioning primers includes a replicase binding site; and
   (3) RNA-dependent RNA polymerase.

* * * * *